United States Patent [19]

Mikulicz et al.

[11] 4,018,841
[45] * Apr. 19, 1977

[54] PROCESS FOR ALKYLATION OF AROMATICS

[75] Inventors: Michael Z. Mikulicz, Palatine; William G. Boney, Rolling Meadows; Bipin V. Vora, Wheeling, all of Ill.

[73] Assignee: UOP Inc., Des Plaines, Ill.

[ * ] Notice: The portion of the term of this patent subsequent to May 18, 1993, has been disclaimed.

[22] Filed: Nov. 13, 1975

[21] Appl. No.: 631,564

Related U.S. Application Data

[63] Continuation-in-part of Ser. No. 520,811, Nov. 4, 1974, Pat. No. 3,957,902.

[52] U.S. Cl. .......................................... 260/671 R
[51] Int. Cl.² ........................................ C07C 15/00
[58] Field of Search ................... 260/671 R, 683.42

[56] References Cited

UNITED STATES PATENTS

| 2,320,629 | 6/1943 | Matuszak | 260/683.42 |
|---|---|---|---|
| 2,379,368 | 6/1945 | Matuszak | 260/683.48 |
| 2,399,368 | 4/1946 | Matuszak | 260/683.48 |
| 3,591,650 | 7/1971 | Mitsak | 260/671 R |
| 3,957,902 | 5/1976 | Mikulicz et al. | 260/683.48 |

*Primary Examiner*—Edward J. Meros
*Assistant Examiner*—Brian E. Hearn
*Attorney, Agent, or Firm*—James R. Hoatson, Jr.; Robert W. Erickson; William H. Page, II

[57] ABSTRACT

Byproduct or waste gases, containing hydrogen fluoride from an HF-catalyzed aromatic alkylation process are contacted with a stream of alkylated aromatics essentially free from hydrogen fluoride. Hydrogen fluoride from the waste gases is absorbed within the alkylated aromatics and is returned to the process therewith. Resulting waste gases are of reduced hydrogen fluoride content, and the loss of hydrogen fluoride upon disposal of these gases is thereby reduced.

1 Claim, 1 Drawing Figure

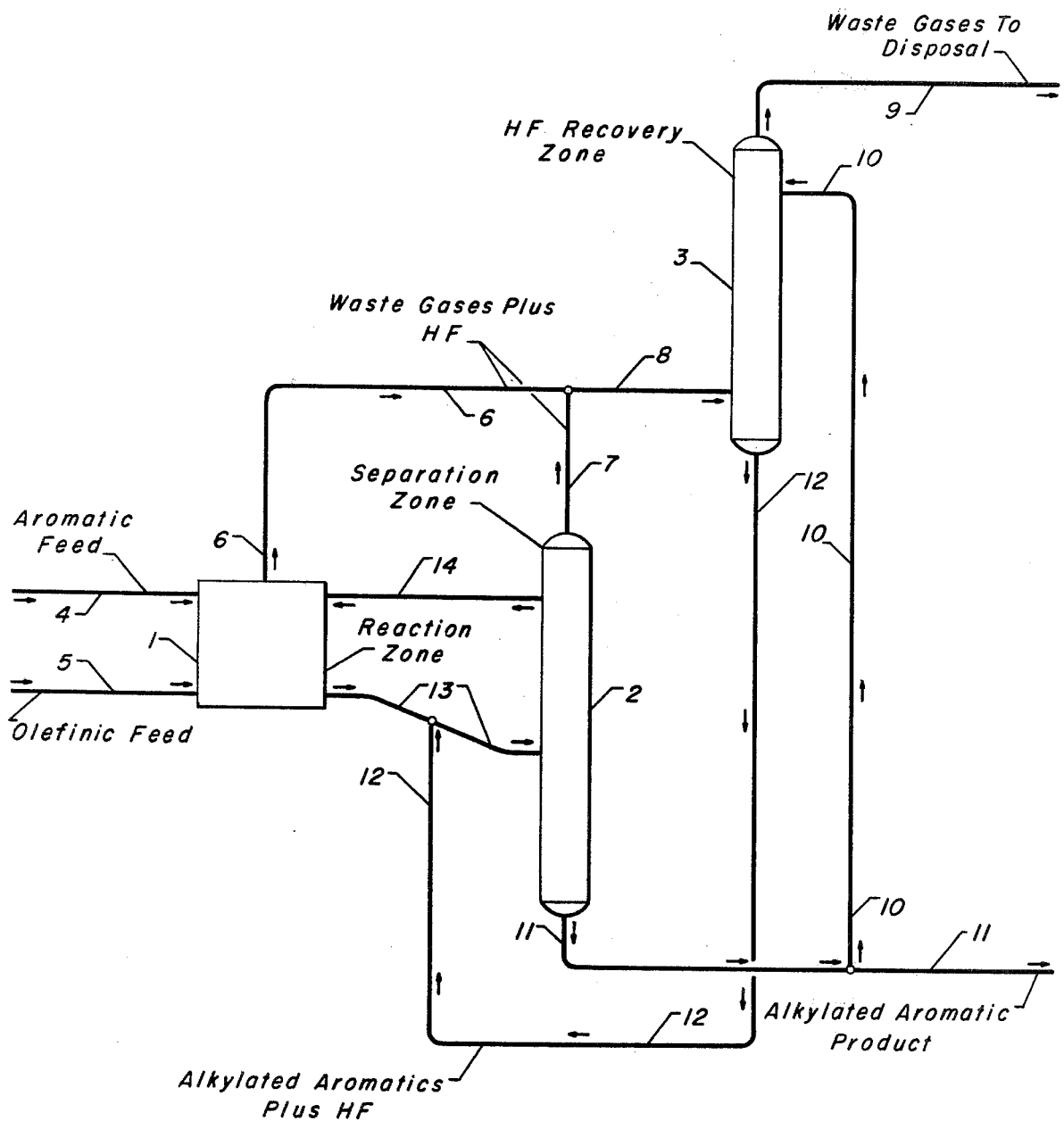

PROCESS FOR ALKYLATION OF AROMATICS

CROSS-REFERENCE TO RELATED APPLICATION

This application is a continuation-in-part of our co-pending application Ser. No. 520,811, filed Nov. 4, 1974 now U.S. Pat. No. 3,957,902, issued on May 18, 1976.

BACKGROUND OF THE INVENTION

1. Field of the Invention

The field of art to which this invention pertains is hydrocarbon processing. It particularly relates to the treatment of byproduct gases from plants for the production of detergent alkylate which utilize hydrogen fluoride as a catalyst.

2. Prior Art

Hydrogen fluoride catalysis finds one of its most important uses in the production of alkylated aromatic compounds. Of particular importance among alkylated aromatics are compounds referred to as detergent alkylate. These compounds are used in conjunction with others to synthesize biodegradable detergents, products of primary importance due to recent ecological considerations. Traditional, non-biodegradable detergents had come into such wide use that the characteristically low rate of their natural decomposition in the earth's surface waters was insufficient to prevent an accumulation of these chemicals in and a concomitant polution of the aqueous environment. Biodegradable detergents, derivatives of n-alkylbenzene, which have much higher rates of natural decomposition, have come into extensive use in order to avoid the contamination of surface waters.

Hydrofluoric acid is a hazardous chemical with properties peculiar to itself which call for special handling and treatment. With improper treatment it can be lethal. For this reason processes for its use must be equipped with systems which effectively prevent its escape into the atmosphere. Common practice in the art is to provide a relief system which collects the effluent of all relief valves and other sources within the process from which hydrogen fluoride may be expected to be released. As is well known in the art, relief valves are commonly fitted to processing zones which may operate at superatmospheric pressures. These valves open and allow an exhaust of material from the process at pressure levels above normal but below that at which structural damage to the processing zones would occur. It is quite common during the cessation or initiation of operation of a process that processing zones are periodically over-pressured. During these periods of overpressure, the associated relief valves open and maintain safe pressure levels by exhausting material from the affected zones. The exhausts from relief valves pass to a relief system which, in current plant designs, carries the exhaust to a treating process wherein the HF contained within the exhaust is chemically altered and made safe for entry into normal waste disposal facilities.

It is common in the art to use a treating process wherein acidic gases from the relief system are countercurrently contacted with an aqueous solution of a metal hydroxide, such as potassium hydroxide, within an elaborate plate-type contact tower. Where KOH is used as the metal hydroxide to treat a gas containing HF the ensuing reaction may be represented by the equation:

$$KOH + HF = KF + HOH.$$

The resulting aqueous KF solution is further contacted with $Ca(OH)_2$ to precipitate $CaF_2$ which is highly insoluble in water. The fluoride precipitate, in the form of a sludge, is then disposed of as waste.

Operators of these prior art processes must replenish the HF lost by chemical treatment of waste gases. The disposal of a precipitate sludge also poses an inconvenience to the processor.

We have found that HF can be recovered from waste gases by the use of a hydrocarbon stream already existing within the process. In this manner HF leaving the process in waste gases is not chemically altered but is returned to the process for further use. HF loss from the process and the HF replenishment which loss necessitates are greatly reduced. The use of elaborate and inconvenient prior art processes involving chemical treatment and disposal of treatment wastes is avoided by use of the present invention.

BRIEF SUMMARY OF THE INVENTION

Our invention involves a process for the recovery of hydrogen fluoride prior to disposal of waste HF alkylation process gases containing hydrogen fluoride. A liquid within the HF process selected to be essentially free of hydrogen fluoride contacts the waste gases, absorbs hydrogen fluoride and returns it to the process. Waste gases disposed of subsequent to this contact are of reduced HF content.

OBJECTS AND EMBODIMENTS

It is an object of this invention to remove hydrogen fluoride from normally vaporous hydrocarbon admixtures containing HF.

Still another object of our invention is to provide an HF-catalyzed hydrocarbon alkylation process with reduced HF loss.

In one embodiment our invention affords an alkylation process which comprises the steps of: (a) reacting olefins with aromatic compounds in contact with hydrogen fluoride catalyst in a reaction zone; (b) separating from the resultant reaction mixture, in a separation zone, an alkylated aromatic product and a stream of unreacted aromatic compounds and hydrogen fluoride; (c) removing from the reaction zone a gaseous stream containing hydrogen fluoride; (d) removing from the separation zone a gaseous stream containing hydrogen fluoride; (e) returning said stream of unreacted aromatic compounds and hydrogen fluoride to said reaction zone; (f) combining said gaseous streams from step (c) and step (d) and contacting said combined gaseous streams with a portion of said alkylated aromatic product to absorb hydrogen fluoride from said combined gaseous streams into said portion of the alkylated aromatic product; and (g) passing said portion of the alkylated aromatic product, containing absorbed hydrogen fluoride from contacting step (f) to the separation zone of step (b).

BRIEF DESCRIPTION OF THE DRAWING

The attached drawing illustrates a particular embodiment of the present invention. Only such details are included as are necessary for a clear understanding of our invention, and no intention is thereby made to unduly limit its scope. Certain items necessary to the operation of the process but unnecessary to its understanding, such as certain process streams, valves, pumps, instrumentation and other equipment have been omitted for the sake of clarity.

The drawing is a schematic representation showing an HF alkylation process having reaction zone 1, separation zone 2 and HF recovery zone 3 in one embodimental configuration of the present invention.

Referring now to the drawing, a first feed stream, comprising olefinic hydrocarbons, enters reaction zone 1 in conduit 5, and a second feed stream, comprising aromatic hydrocarbons, enters reaction zone 1 in conduit 4.

A mixture of HF, alkylated aromatics and unreacted aromatics exits reaction zone 1 in conduit 13 and passes to separation zone 2 where an alkylated aromatic product is separated from the mixture and exits separation zone 2 in conduit 11. HF and unreacted aromatics exit separation zone 2 in conduit 14 and return to the reaction zone.

Waste gases, containing HF, exit reaction zone 1 in conduit 6 and combine with similar waste gases exiting separation zone 2 in conduit 7. The combined waste gases pass to HF recovery zone 3 in conduit 8.

A portion of the alkylated aromatic product exiting the separation zone in conduit 11 passes to HF recovery zone 3 in conduit 10. Alkylated aromatics entering the HF recovery zone in conduit 10 absorb HF from the waste gas-HF mixture within the HF recovery zone. Alkylated aromatics and absorbed HF exit the HF recovery zone in conduit 12 and pass to conduit 13 wherein they are conducted to separation zone 2. Waste gases, substantially free from HF, exit the HF recovery zone in conduit 9.

DETAILED DESCRIPTION OF THE INVENTION

Hydrofluoric acid is particularly dangerous because of its effect upon all living body tissues. It is harmful in practically any concentration in either liquid or vapor form. In solution, hydrofluoric acid breaks down into hydrogen and fluorine which are present as what are known as hydrogen ions and fluorine ions. Hydrofluoric acid causes a surface burn to bodily tissues through the action of the hydrogen ions. In addition, the fluorine ions penetrate below the surface and continue to attack and destroy tissue and bone until they are precipitated as magnesium or calcium fluoride by the action of magnesium or calcium compounds present in the body or administered in medical treatments. The fluorine ions effect deep seated, ulcerous sores which commonly resist therapeutic efforts. The effect of the acid upon skin and mucus tissue is to cause extreme pain which often occurs only after the acid has been absorbed below the surface, such that washing is largely ineffective. This effect is commonly known as "delayed-action burn".

Because of the character of these acids it is essential that they not be released into the atmosphere. For this reason elaborate and costly systems are designed into process plants using HF to collect the exhaust of waste gases from the process and remove the HF from it before conduction to waste disposal facilities.

Byproduct, or waste, gases from hydrocarbon processes are comprised, primarily, of relief, vent and purge gases. Relief gases result from the opening of relief valves within the plant. When a relief valve associated with an acid-bearing processing zone opens, it exhausts acid gases into the relief system which conducts the gases to treating facilities for removal of acidic components. Vent and purge gases result, respectively, from the depressuring and cleansing of unit operations equipment, often in preparation for mechanical maintenance. The acidic materials remaining within a broken pump, for example, are vented and purged from the pump through special conduits which conduct the acidic materials and the purging medium to the relief system.

Traditional processes used for treatment of relief, vent and purge gases for removal of HF generally involve contact of the gases with a liquid treating medium and subsequent regeneration of the treating medium. The resultant waste product, usually in the form of a precipitate sludge of a metal fluoride is inconvenient to handle and dispose. Common practice in the art is to use special vehicles, equipped with vacuum actuated retrieval systems, to aspirate the sludge into tanks for its translation to a place of disposal. The cost and complexity of operation of these prior art HF removal processes, combined with the irrecoverable loss of HF in the sludge which they produce, make them a source of bother and inconvenience to operators of HF alkylation process plants.

Our invention provides an HF alkylation process which is an advance over the prior art by virtue of the inclusion of novel steps for recovery of HF from byproduct or waste gases.

In the process of our invention aromatic compounds are alkylated by olefins. Aromatic compounds suitable for use therein are substituted or unsubstituted aromatic hydrocarbons such as benzene, toluene, xylenes, naphthalene, tetralin, phenanthrene, anthracene and the like. Olefins which may be suitably used in our invention include $C_3$-$C_{20}$ olefinic hydrocarbons. Hydrogen fluoride, HF, is used as the alkylation catalyst. A preferred alkylation catalyst contains from 80–90% hydrogen fluoride, less than 2% water and soluble organic material as the remainder.

The process of our invention comprises a reaction zone, a separation zone and an HF recovery zone. The reaction zone may be any of the designs well known in the art which provides for: contact of aromatic feeds with olefin feeds and with HF alkylation catalyst, separation and recycle of unreacted aromatic compounds from the resultant reaction mixture, rejection of unwanted feed components, etc. Alkylation conditions to be maintained within the reaction zone include a temperature of from about 0° to about 150° F, and a pressure of about 1 atmosphere to about 40 atmospheres. A preferred range of temperature is from about 30° to about 100° F.

The separation zone of the process receives a reaction mixture stream from the reaction zone and separates it into an alkylated aromatic product and one or more other streams which may contain: unreacted aromatics and HF to be returned to the reaction zone for further participation therein; undesirable feed components for rejection from the process, such as paraffins which unavoidably accompany an olefin stream; etc. The separation zone may be any one of the well known devices for separation of alklation reaction mixtures, such as a stripping tower.

A characteristic of HF alkylation plants is that they produce waste gases from their processing zones, as aforesaid. These waste gases are gaseous streams containing hydrogen fluoride. Waste gases from the reaction zone and the separation zone of the process of our invention pass to the HF recovery zone where HF, a soluble component of the waste gas mixture, is dissolved in a liquid. The liquid used is a portion of the alkylated aromatic product. This liquid is returned to the separation zone after absorption of HF in the HF recovery zone.

The HF recovery zone may be a tower filled with solid packing material, a tower containing a number of sieve or bubble-cap plates, or an empty tower into which the absorbing liquid is sprayed. Selection of the type and size of tower used depends upon the individual plant, according to the projected or actual waste gas rate and composition, and is well within the technical abilities of those skilled in the art. A preferred configuration provides countercurrent flows of liquid and waste gas within the HF recovery zone.

The operating conditions which may be used in the HF recovery zone of the process of our invention include a temperature of from about 35° to about 200° F and a pressure of from about 0 psig to about 500 psig. Preferred temperatures are those lowest in the acceptable range. Pressure is preferably maintained as high as possible within the acceptable range.

Sufficient contact between liquid and waste gas within the HF recovery zone is provided such that waste gas exiting the HF recovery zone is essentially HF-free.

In one embodiment of our invention 10,886 barrels per day of feeds comprising paraffins, $C_{10}$ to $C_{14}$ olefins and benzene enter the reaction zone. The feeds, if mixed would have approximately the following composition: 8 mole % benzene, 8 mole % $C_{10}$ to $C_{14}$ olefins, 84 mole % $C_{10}$ to $C_{14}$ paraffins. 326 barrels per day of alkylated aromatics are withdrawn from the separation zone as an alkylated aromatic product, and 2000 barrels per day of alkylated aromatics exit the separation zone and are supplied to the HF recovery zone for contact with waste gases. Waste gases leaving the HF recovery zone, having contacted the 2000 barrels per stream day of alkylated hydrocarbons, are essentially HF-free. Operating conditions within the HF recovery zone are a pressure of 25 psig and a temperature of 110° F. The 2000 barrels per day of alkylated aromatics plus absorbed HF return from the HF recovery zone to the separation zone of the process.

We claim as our invention:

1. An alkylation process which comprises the steps of:
   a. reacting olefins with aromatic compounds in contact with hydrogen fluoride catalyst in a reaction zone;
   b. separating from the resultant reaction mixture, in a separation zone, an alkylated aromatic product and a stream of unreacted aromatic compounds and hydrogen fluoride;
   c. removing from the reaction zone a gaseous stream containing hydrogen fluoride;
   d. removing from the separation zone a gaseous stream containing hydrogen fluoride;
   e. returning said stream of unreacted aromatic compounds and hydrogen fluoride to said reaction zone;
   f. combining said gaseous streams from step (c) and step (d) and contacting said combined gaseous streams with a portion of said alklated aromatic product to absorb hydrogen fluoride from said combined gaseous streams into said portion of the alkylated aromatic product; and
   g. passing said portion of the alkylated aromatic product, containing absorbed hydrogen fluoride from contacting step (f) to the separation zone of step (b).

* * * * *